(12) United States Patent
James

(10) Patent No.: US 8,940,021 B2
(45) Date of Patent: *Jan. 27, 2015

(54) MULTI-AXIAL CROSS CONNECTOR

(71) Applicant: Spine Wave, Inc., Shelton, CT (US)

(72) Inventor: Anthony James, Bartlett, TN (US)

(73) Assignee: Spine Wave, Inc., Shelton, CT (US)

( * ) Notice: Subject to any disclaimer, the term of this patent is extended or adjusted under 35 U.S.C. 154(b) by 169 days.

This patent is subject to a terminal disclaimer.

(21) Appl. No.: 13/761,342

(22) Filed: Feb. 7, 2013

(65) Prior Publication Data

US 2013/0150888 A1      Jun. 13, 2013

Related U.S. Application Data

(62) Division of application No. 12/780,619, filed on May 14, 2010, now Pat. No. 8,372,120.

(60) Provisional application No. 61/179,790, filed on May 20, 2009.

(51) Int. Cl.
*A61B 17/70* (2006.01)

(52) U.S. Cl.
CPC .................................. *A61B 17/7052* (2013.01)
USPC .......................................... 606/253; 606/250

(58) Field of Classification Search
USPC .......................... 606/250–253, 260, 277, 278
See application file for complete search history.

(56) References Cited

U.S. PATENT DOCUMENTS

| | | |
|---|---|---|
| 5,443,465 A | 8/1995 | Pennig |
| 5,522,816 A | 6/1996 | Dinello et al. |
| 5,531,747 A | 7/1996 | Ray |
| 5,569,246 A | 10/1996 | Ojima et al. |
| 5,624,442 A | 4/1997 | Mellinger et al. |
| 5,667,507 A | 9/1997 | Corin et al. |
| 5,709,684 A | 1/1998 | Errico et al. |
| 5,752,955 A | 5/1998 | Errico |
| 5,947,966 A | 9/1999 | Drewry et al. |
| 5,984,923 A | 11/1999 | Breard |
| 6,187,005 B1 | 2/2001 | Brace et al. |
| 6,217,578 B1 | 4/2001 | Crozet et al. |
| 6,238,396 B1 | 5/2001 | Lombardo |
| 6,273,914 B1 | 8/2001 | Papas |
| 6,379,354 B1 | 4/2002 | Rogozinski |
| 6,402,751 B1 | 6/2002 | Hoeck et al. |
| 6,488,682 B2 | 12/2002 | Kikuchi et al. |
| 6,554,832 B2 | 4/2003 | Shluzas |

(Continued)

FOREIGN PATENT DOCUMENTS

| | | |
|---|---|---|
| DE | 9402695 | 5/1994 |
| FR | 2 732 887 A1 | 10/1996 |

*Primary Examiner* — Pedro Philogene
*Assistant Examiner* — Lynnsy Summitt
(74) *Attorney, Agent, or Firm* — Hoffmann & Baron, LLP

(57) ABSTRACT

A cross connector for attachment between two spinal implants comprises a first element having one end and an opposite end configured for engaging one of the two spinal implants, a second element having one end and an opposite end configured for engaging the other of the two spinal implants, an engagement mechanism between the one end of each of the first and second elements, and a locking element for locking the two elements together at the respective one end. The engagement mechanism includes an interface configured to permit relative pivoting between the first element and the second element about at least two non-parallel axes.

4 Claims, 6 Drawing Sheets

(56) References Cited

U.S. PATENT DOCUMENTS

| | | |
|---|---|---|
| 6,626,904 B1 | 9/2003 | Jammet et al. |
| 6,736,817 B2 | 5/2004 | Troxell et al. |
| 6,802,844 B2 | 10/2004 | Ferree |
| 6,872,208 B1 | 3/2005 | McBride et al. |
| 6,887,241 B1 | 5/2005 | McBride et al. |
| 7,104,993 B2 | 9/2006 | Baynham et al. |
| 7,137,986 B2 | 11/2006 | Troxell et al. |
| 7,160,301 B2 | 1/2007 | Cordaro |
| 7,207,992 B2 | 4/2007 | Ritland |
| 7,481,827 B2 | 1/2009 | Ryan et al. |
| 7,485,132 B1 | 2/2009 | McBride et al. |
| 7,695,499 B2 | 4/2010 | Morrison et al. |
| 8,361,117 B2 * | 1/2013 | Michielli et al. ............... 606/253 |
| 2001/0010000 A1 | 7/2001 | Gertzbein et al. |
| 2002/0143330 A1 | 10/2002 | Shluzas |
| 2002/0169448 A1 | 11/2002 | Vanacker |
| 2003/0114853 A1 * | 6/2003 | Burgess et al. ............... 606/61 |
| 2004/0116928 A1 | 6/2004 | Young et al. |
| 2004/0133203 A1 | 7/2004 | Young et al. |
| 2005/0010222 A1 | 1/2005 | Cordaro |
| 2005/0080416 A1 | 4/2005 | Ryan et al. |
| 2005/0090821 A1 | 4/2005 | Berrevoets et al. |
| 2005/0228377 A1 | 10/2005 | Chao et al. |
| 2006/0058789 A1 | 3/2006 | Kim et al. |
| 2006/0064093 A1 | 3/2006 | Thramann et al. |
| 2006/0142758 A1 | 6/2006 | Petit |
| 2006/0217710 A1 | 9/2006 | Abdou |
| 2006/0259038 A1 | 11/2006 | Cordaro |
| 2006/0271051 A1 | 11/2006 | Berrevoets et al. |
| 2006/0276794 A1 | 12/2006 | Stern |
| 2007/0016197 A1 | 1/2007 | Woods et al. |
| 2007/0198014 A1 | 8/2007 | Graf et al. |
| 2007/0213721 A1 | 9/2007 | Markworth et al. |
| 2007/0213723 A1 | 9/2007 | Markworth et al. |
| 2007/0225713 A1 * | 9/2007 | Altarac et al. ............... 606/64 |
| 2007/0233090 A1 | 10/2007 | Naifeh et al. |
| 2007/0233091 A1 | 10/2007 | Naifeh et al. |
| 2007/0250061 A1 | 10/2007 | Chin et al. |
| 2007/0270843 A1 | 11/2007 | Matthis et al. |
| 2008/0015588 A1 | 1/2008 | Hawkes |
| 2008/0109039 A1 | 5/2008 | Michielli et al. |
| 2008/0119857 A1 | 5/2008 | Potash et al. |
| 2008/0140124 A1 | 6/2008 | Jeon et al. |
| 2008/0172093 A1 | 7/2008 | Nilsson |
| 2008/0183215 A1 | 7/2008 | Altarac et al. |
| 2008/0306538 A1 | 12/2008 | Moore et al. |
| 2009/0043339 A1 | 2/2009 | Tepper et al. |
| 2009/0105763 A1 | 4/2009 | Kirschman |
| 2009/0105765 A1 | 4/2009 | Strnad |
| 2009/0177232 A1 | 7/2009 | Kiester |

* cited by examiner

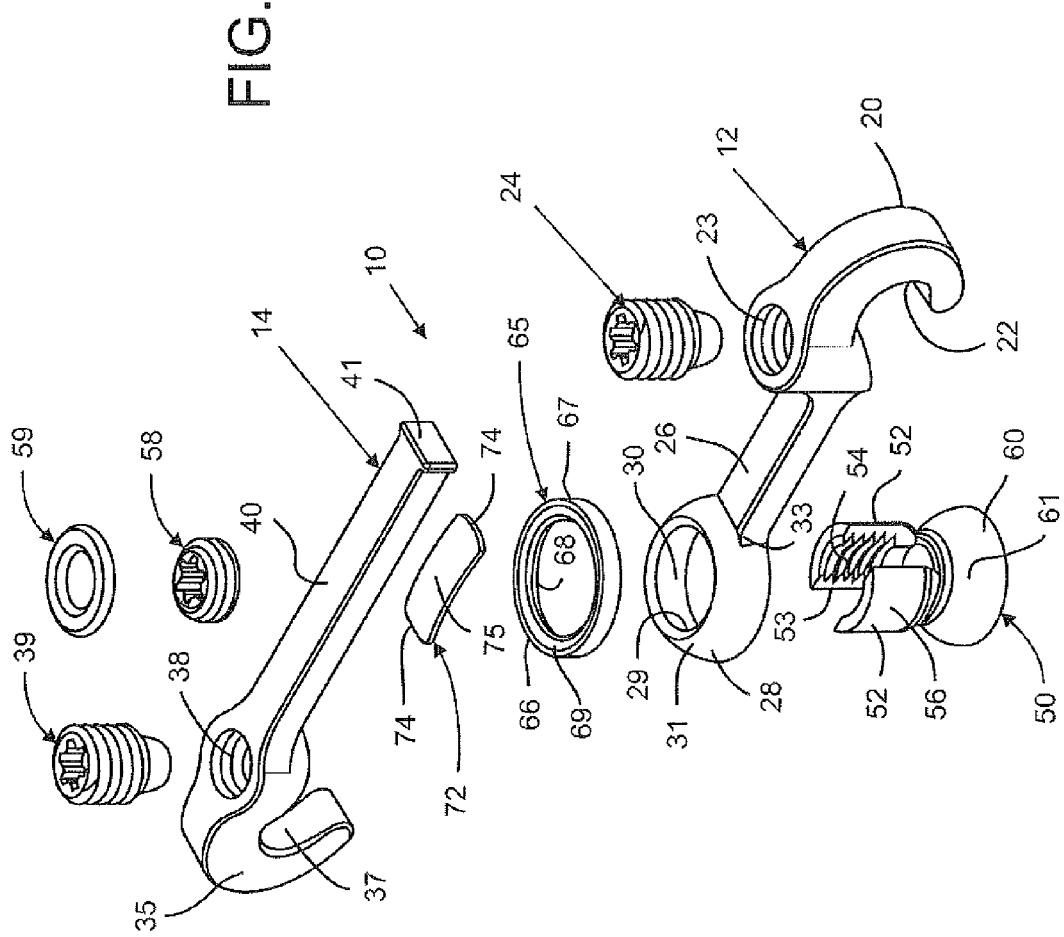

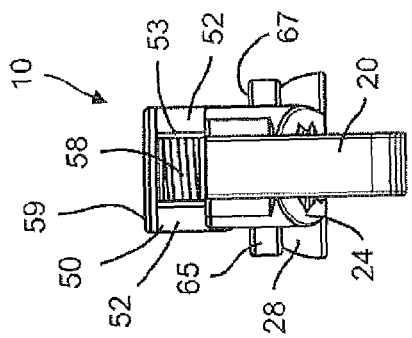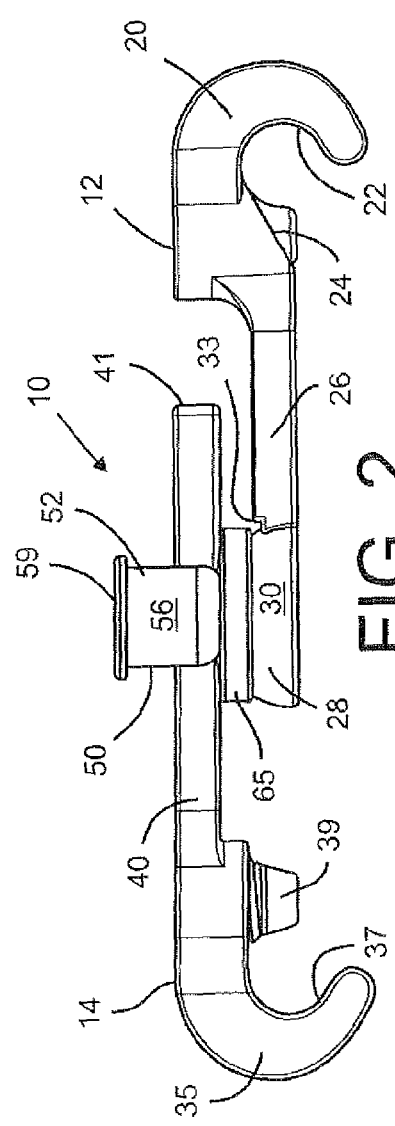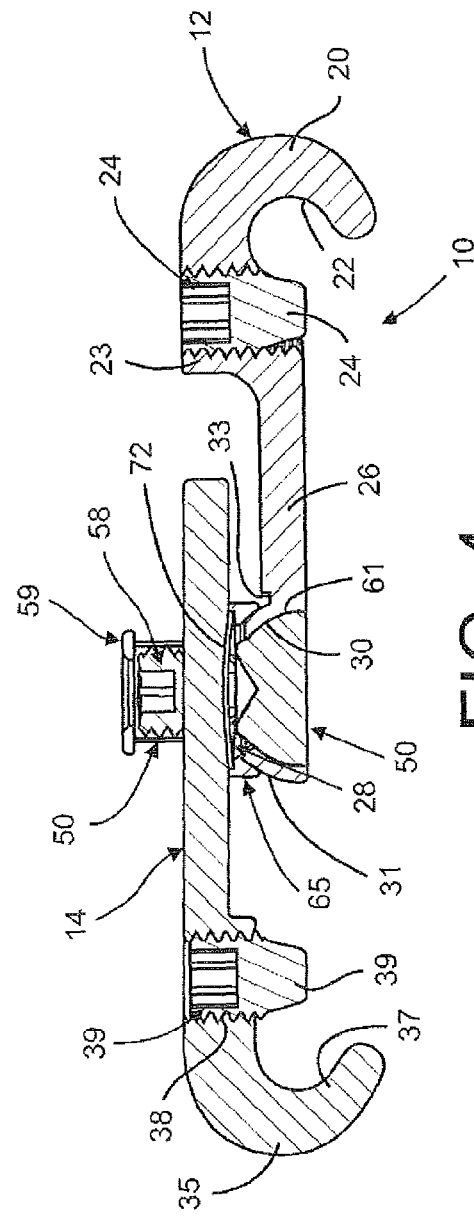

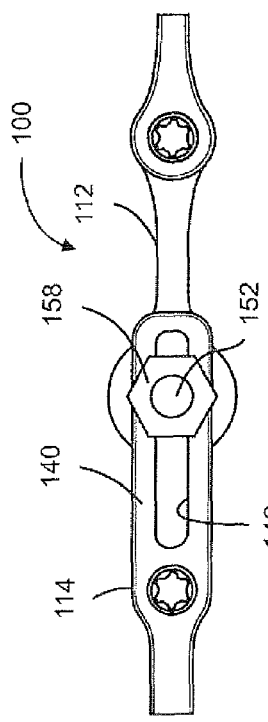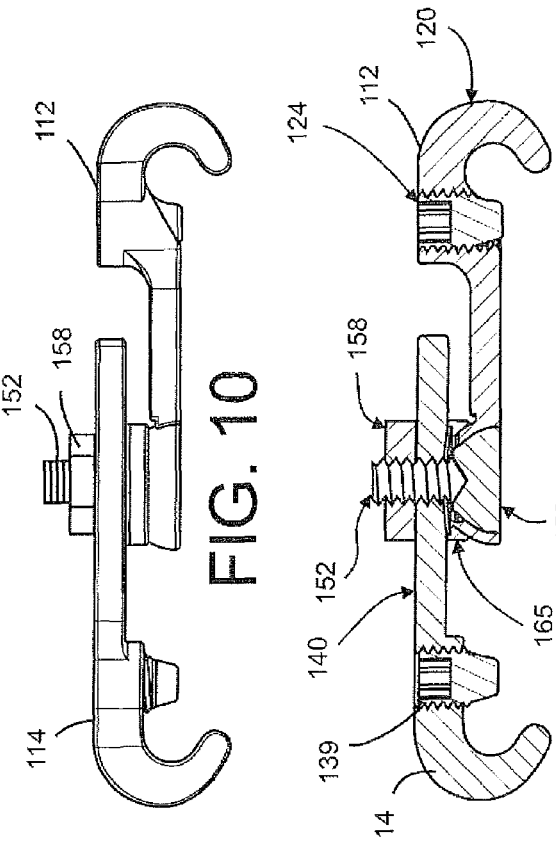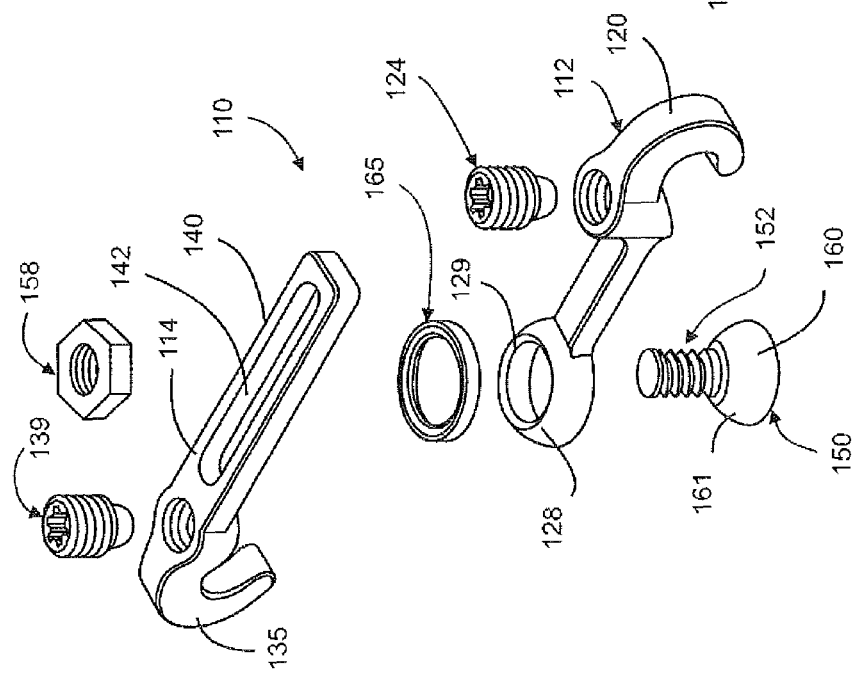

MULTI-AXIAL CROSS CONNECTOR

This application is a divisional application of U.S. application Ser. No. 17/780,619, filed May 14, 2010, now U.S. Pat. No. 8,372,120, which claims priority to U.S. Provisional Application No. 61,179,790, filed May 20, 2009, the entire contents of these application being incorporated by reference herein.

BACKGROUND

A cross connector for a spinal construct is provided that is capable of variable angular orientations and rotations about multiple axes.

Cross connectors are known to provide transverse rigidity to a dual rod construct in a patient. Cross connectors are typically fastened to two parallel rods spanning a length of the spine on opposite sides of the median plane. Cross connectors in general can be clumsy to place on the rods in a rod/screw construct, a difficulty that is enhanced by the limited ability to manipulate or position the typical cross connector. For instance, certain cross connectors only permit relative movement of rod-engaging ends towards or apart from each other. In some cases the cross connector may permit relative rotation between the bar-engaging ends within a single plane parallel to the axis of the cross connector. Other cross connector designs allow rotation of a rod-engaging end about its own longitudinal axis.

However, the spinal anatomy varies with the patient and the condition to be treated. As such, there is a need for a cross connector that provides enhanced degrees of freedom to address the wide range of treatment protocols that may be encountered.

SUMMARY

A cross connector for attachment between two spinal implants comprises a first element having one end and an opposite end configured for engaging one of the two spinal implants, a second element having one end and an opposite end configured for engaging the other of the two spinal implants, an engagement mechanism between the one end of each of the first and second elements, and a locking element for locking the two elements together at the respective one end. The engagement mechanism includes an interface configured to permit relative pivoting between the first element and the second element about at least two non-parallel axes. The interface may also be configured to permit relative linear movement between the first and second elements. In one aspect, the interface includes a spherical interface that permits relative angulation or pivoting in the yaw, pitch and roll degrees of freedom.

DESCRIPTION OF THE FIGURES

FIG. 1 is an exploded perspective view of one arrangement of a transverse connector assembly described herein.

FIG. 2 is a side view of the transverse connector assembly shown in FIG. 1.

FIG. 3 is an end view of the transverse connector assembly shown in FIG. 1.

FIG. 4 is a side cross-sectional view of the transverse connector assembly in FIG. 2.

FIG. 8 is an exploded perspective view of a second arrangement of a transverse connector assembly described herein.

FIG. 9 is a top view of the transverse connector assembly shown in FIG. 8.

FIG. 10 is side view of the transverse connector assembly shown in FIG. 8.

FIG. 11 is a side cross-sectional view of the transverse connector assembly shown in FIG. 8.

DESCRIPTION OF THE EMBODIMENTS

Figure 5:
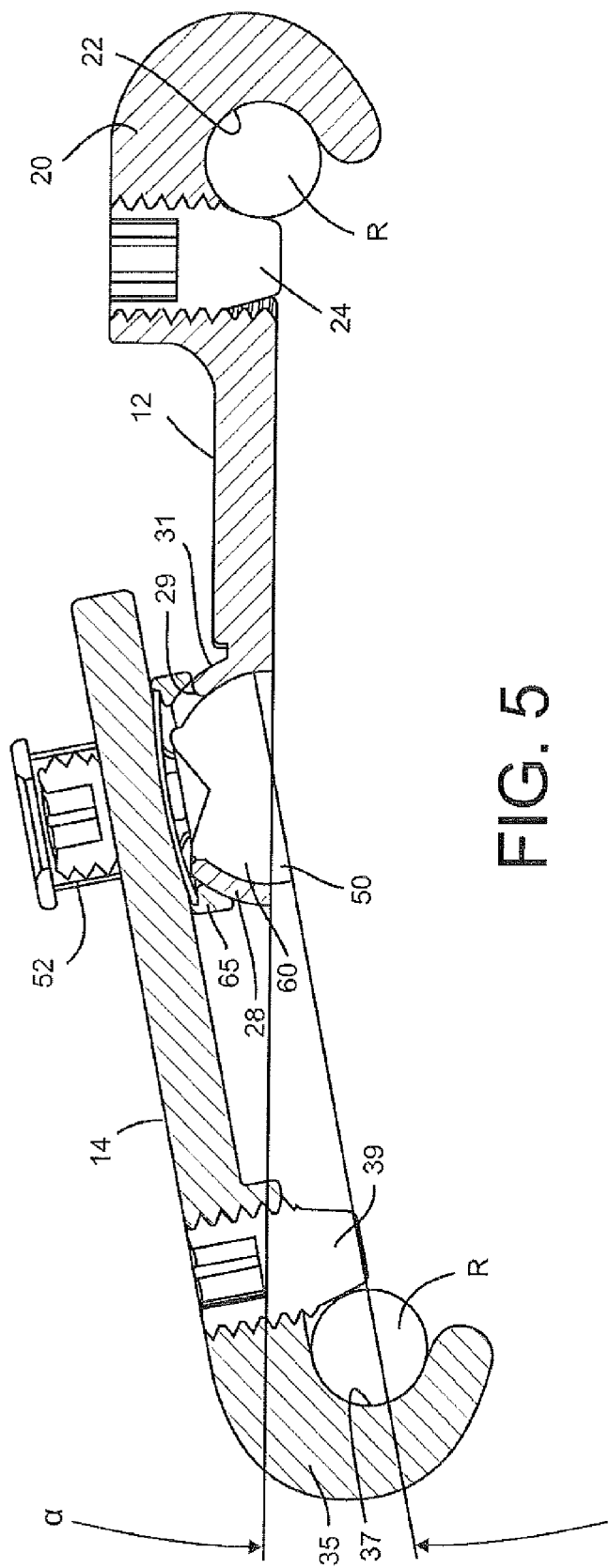
FIG. 5 is a side partial cross-sectional view of the transverse connector assembly shown in FIGS. 1-4 with the adjustable element at a pitch angle in a first direction of pivoting relative to the stationary element of the connector assembly.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A cross connector assembly 10 includes a first "stationary" element 12 and a second "adjustable" element 14, as shown in FIGS. 1-4. For the purposes of the present description, the designation of one element as "stationary" and the other as "adjustable" is arbitrary, with the understanding that the intent is to describe that the two elements are translatable and pivotable relative to each other, as described herein. The stationary element 12 includes an engagement end 20 which, in the illustrated embodiment, defines a rod opening 22 sized to engage a spinal implant, such as an elongated spinal rod R (see, FIG. 5). In this embodiment, the cross connector assembly is adapted to attach to spinal rods positioned on either side of the spinal midline and spanning a length of the spine in a typical rod-based fixation construct. However, it is contemplated that the engagement end 20 may be configured to engage other spinal elements, such as bone plates spanning two or more vertebrae or a bone screw or hook engaged to a vertebral body. In the embodiment shown in FIG. 1, the rod opening is intersected by a set screw bore 23 that receives a set screw 24 in a conventional manner. The set screw is threaded into the bore 23 to capture a rod disposed within the rod opening 22. Of course, other means for fixing the stationary element 12 to a spinal implant are contemplated.

The stationary element 12 further includes an elongated bar 26 that extends axially from engagement end 20 and terminates in a flange defining an opposite cup end 28. The bar 26 and end 28 are sized to span a portion of the lateral distance between the spinal implants or rods in the fixation construct. The cup end 28 defines an opening 29 therethrough. The upper surface 30 of the cup end is spherical to form an annular spherical surface capable of articulation or pivoting in multiple degrees of freedom or about multiple separate axes.

The cross connector assembly 10 further includes an adjustable element 14 that incorporates an engagement end 35. The engagement end 35 may be similar to the engagement end of the stationary element 12 in that it includes a rod opening 37, set screw bore 38 and set screw 39 for clamping to an elongated spinal rod. Of course, like the end 20, the engagement end 35 may be configured to engage a different spinal implant, such as a bone plate, bone screw or hook. It is further contemplated that the engagement ends 20 and 35 may be differently configured depending upon the desired form of the fixation construct. The adjustable element 14 further includes an extension member such as elongated bar 40 extending axially from the engagement end 35 and terminating in an opposite bar end 41. The bar 40 may be non-circular, and more particularly rectangular as depicted in FIG. 1. The bar end 41 may be larger than the bar 40 to restrict separation of the stationary and adjustable elements 12, 14 when coupled as described below.

The cross connector assembly 10 incorporates an engagement mechanism between the two elements that provides a multiple degree of freedom articulating interface between the stationary element 12 and the adjustable element 14. Thus, in one embodiment, the assembly 10 includes a pivot element defined at its upper portion by a yoke element 50 that includes two opposing branches 52 projecting upward from a base 60 at the lower portion of the pivot element. The branches 52 define a slot 53 therebetween that is sized to receive the elongated bar 40 of the adjustable element 14. The bar end 41 of the adjustable element is preferably sized so that it cannot pass through the slot 53 when the bar is received within the slot to thus prevent disengagement of the two cross connector elements when the elements are moved apart.

Figure 7:
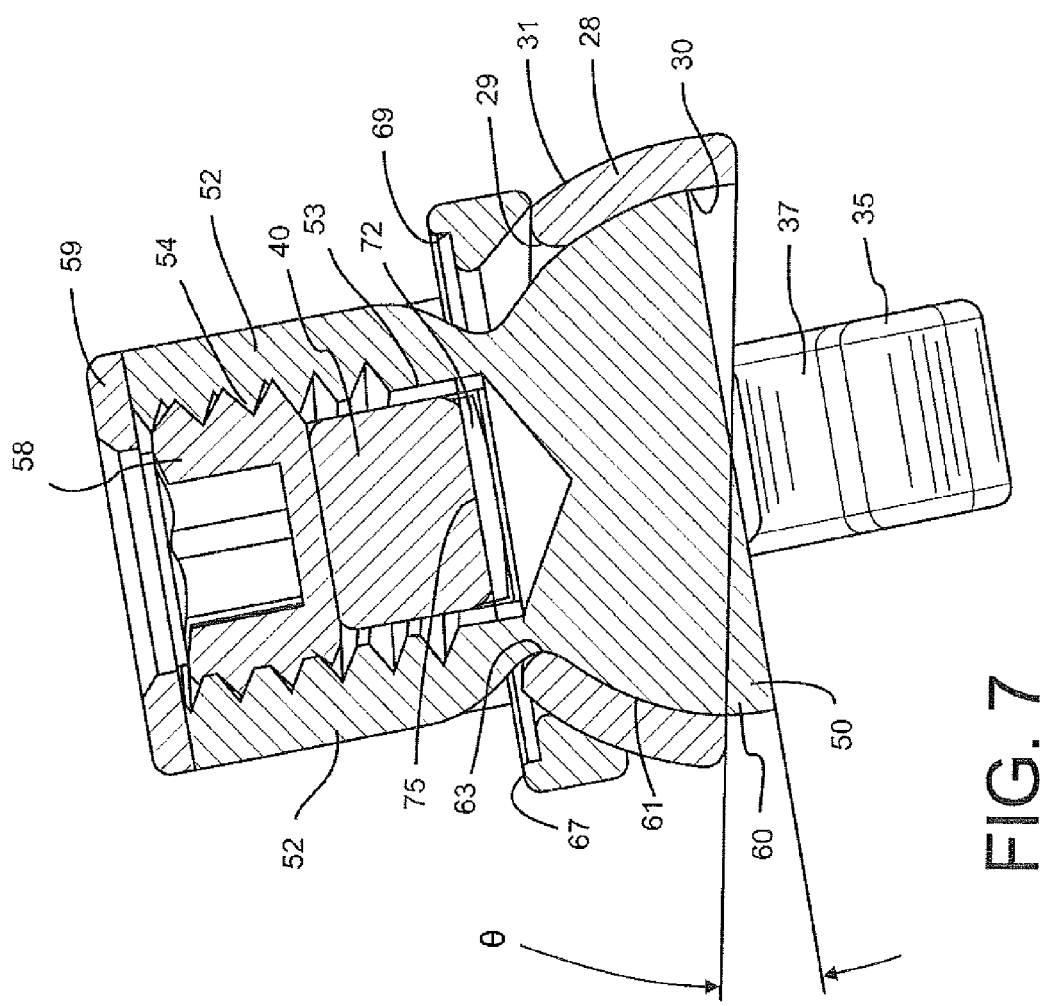
FIG. 7 is an end partial cross-sectional view of the transverse connector assembly shown in FIGS. 1-4 with the adjustable element at a roll angle relative to the stationary element of the connector assembly.

The branches 52 extend generally parallel to the central axis of the yoke and further define an inner threaded surface 54 for receiving a set screw 58. As best seen in FIGS. 4 and 7, the set screw 58 is threaded into the branches 52 to bear against the elongated bar 40. The set screw 58 is sized so that it can be wholly contained within the branches 52 of the yoke element 50 while only loosely retaining the elongate bar 40 within the slot 53. A locking ring 59 may be provided on the top of the branches 52 to trap the set screw 58 within the branches and to prevent the set screw 58 from backing out from the yoke element 50. The locking ring 59 includes an opening to permit access to the set screw by a conventional driving tool. Although an inner thread and set screw arrangement is described for clamping the rod within the yoke, other clamping or fixation mechanisms are contemplated. For instance, in lieu of the inner threads the yoke may be provided with exterior threads on the branches that are engaged by an internally threaded nut, rather than the externally threaded set screw.

The outer surface 56 of the branches 52 of the yoke element 50 defines a diameter that is sized to fit through the diameter of opening 29 in the cup end 28 of the stationary element 12. Likewise, the upper surface 61 of the base 60 is a partially spherical bearing surface forming an articulating joint with the spherical lower bearing surface 30 of the cup end 28. It can be appreciated that the yoke element 50 can swivel or pivot in multiple directions or degrees of freedom, or about at least three independent axes, relative to the cup end 28 so that the branches 52 can be oriented at a range of angles relative to the bar 26 of the stationary element 12.

As shown in FIG. 4, the yoke element 50 extends through the opening 29 in the cup end 28 of the stationary element 12. The adjustable element 14 is then positioned within the slot 53 between the branches 52 so that the adjustable element 14 is positioned above and linked to the stationary element 12. In order to facilitate full articulation and eventual locking engagement of the two elements 12 and 14, the assembly 10 may be provided with a locking collar 65 that fits over the branches 52 of the yoke element 50. The locking collar 65 is disposed between upper surface 31 of the cup end 28 and the elongated bar 40 of the adjustable element 14. The inner diameter 66 of the locking collar 65 is thus sized to receive the branches 52 therethrough. The locking collar has a generally flat upper surface 67 for flush contact with the generally rectangular elongated bar 40. The lower surface 68 of the collar 65 is spherical to form an articulating joint with the spherical upper surface 31 of the cup end 28. Alternatively, the upper surface 67 of the collar 65 may have a different configuration for engagement with the bar 40 of the adjustable element 14. For instance, if the bar 40 is circular, rather than rectangular, the upper surface may incorporate a circular notch for receiving the circular bar therein. If the cross-section of the bar 40 is rectangular, polygonal or other non-circular geometry, the bar 40 will be slidably but non-rotatably coupled to the yoke element 50.

The locking collar 65 further defines in one arrangement of the assembly 10 a circumferential recess 69 at the upper surface. The recess receives a leaf spring 72 so that the spring is situated between the elongated bar 40 and the locking collar 65. In the illustrated embodiment, the leaf spring 72 is generally rectangular so that it spans the diameter of the locking collar with its ends 74 situated within the recess 69. The width of the leaf spring is sized so that the branches 52 of the yoke 50 can pass between the leaf spring and the cup 28 at the opening 29. The upper surface 75 of the leaf spring contacts the elongated bar 40. The leaf spring 72 is calibrated to provide some resistance or friction to hold the connector assembly 10 in a particular orientation while permitting continued articulation or pivoting until the assembly is finally clamped. Thus, the leaf spring 72 reacts against the locking collar 65 (which reacts against the cup end 28) to push the bar 40 upward into the set screw 58. Pushing the set screw 58 upward pulls the branches 52 of the yoke element 50 with it, which thereby pulls the base 60 of the yoke element into the lower surface 30 of the cup end 28. The result is a loose frictional engagement between the base 60 and the cup end 28 that tends to tentatively hold the yoke element 50 at whatever orientation it is manually moved to.

Once the cross connector assembly 10 is arranged in its desired orientation with the engagement ends 20 and 35 engaged to a corresponding spinal element, the set screw 58 can be fully tightened within the yoke element 50. As the set screw 58 is advanced into the inner threaded surface 54 of the yoke element, the screw pushes the bar 40 downward and pulls the yoke element 50 upward, thereby compressively locking the bar element, leaf spring, locking collar and cup end between the set screw and the base of the yoke element.

The spherical engagement mechanism provided by the cup end 28 and yoke element 50 permits articulation or pivoting of the two elements 12 and 14 in multiple degrees of freedom or along multiple separate axes. Thus, as shown in FIG. 5, the adjustable element 14 can be pivoted downward at a pitch angle $\alpha$ relative to the stationary element 12, with the pivoting occurring about an axis projecting from the page. The yoke element 50 can pivot downward until the branches 52 contact the circumferential wall of the opening 29 in the cup end 28. As best shown in FIG. 7, the yoke element 50 may incorporate a general rounded transition 63 between the base 60 and the branches 52, and it is this transition that contacts the cup end opening 29 to limit the rotation or pivoting of the yoke element. In one specific approach, the transition 63 and opening 29 are sized relative to each other so that the adjustable element 14 can pivot to a downward pitch angle $\alpha$ of about eleven degrees.

Figure 6:
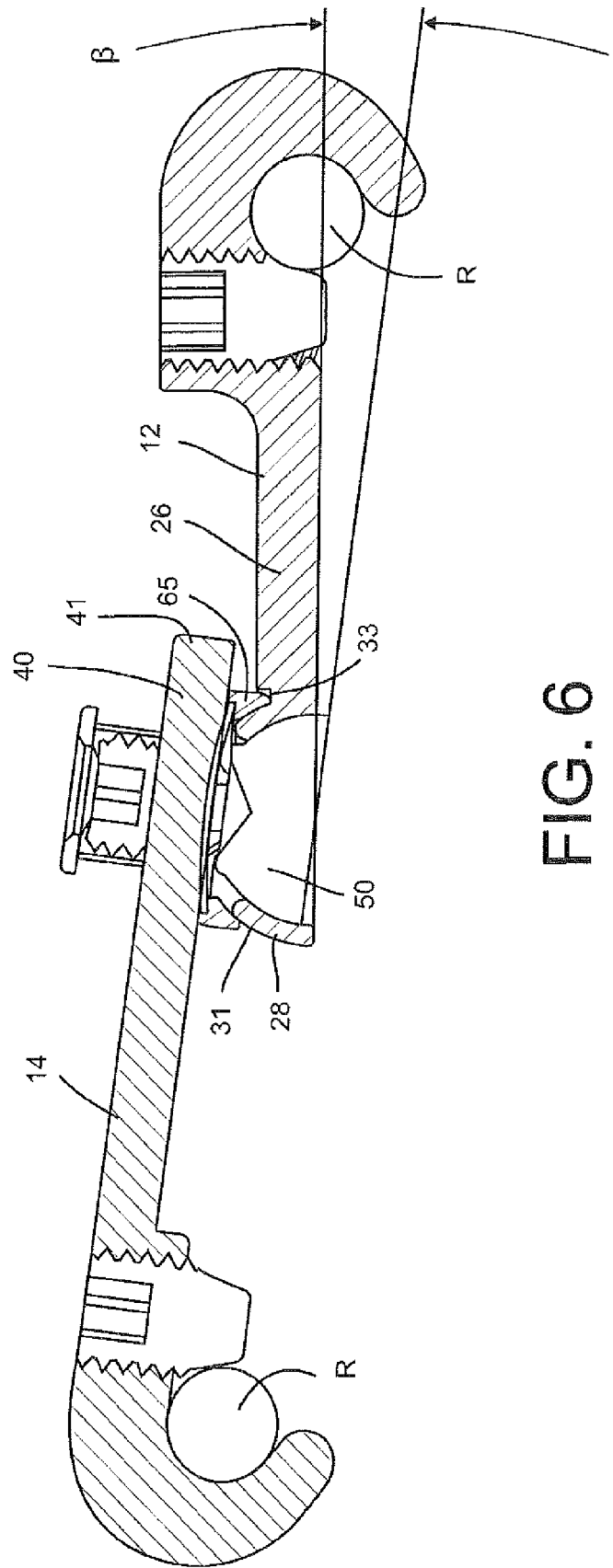
FIG. 6 is a side partial cross-sectional view of the transverse connector assembly shown in FIGS. 1-4 with the adjustable element at a pitch angle in a second direction of pivoting relative to the stationary element of the connector assembly.

However, the upward pitch angle, depicted in FIG. 6, is generally more limited than the downward pitch angle limit. In part, the upward pitch angle is limited by the extent that the elongated bar 40 projects through the yoke element 50 toward the elongated bar 26 of the stationary element 12. In other words, if the bar 40 is pushed farther through the yoke than depicted in FIG. 6, the bar end 41 will contact the stationary element bar 26 to prevent further pivoting of the adjustable element 14.

In the instance in which the bar end 41 provides adequate clearance for full upward pivoting, the amount of pivoting is then limited by contact between the locking collar 65 and the bar 26. In order to reduce the profile of the cross connector assembly 10, it is preferable that the upper surface 31 of the cup end 28 have as little prominence relative to the bar 26 as possible. However, this lower prominence may potentially limit how far the locking collar can pivot. In order to increase the pivot angle of the locking collar relative to the cup end, the bar 26 defines a notch 33 adjacent the cup end, as shown in FIG. 6. This notch provides clearance to accept the edge of the locking collar 65 as the collar articulates on the upper surface 31 below the plane of the elongated bar 26. The amount of upward pivoting, or the angle $\beta$, is thus in this instance a function of the depth of the notch 33. In one specific arrangement, the notch and locking collar are configured for a maximum upward pivot angle $\beta$ of about seven degrees.

The cross connector assembly 10 further permits pivoting in a roll degree of freedom—i.e., in a plane perpendicular to the plane of the pitch rotation shown in FIGS. 5-, or about an axis that is perpendicular to the axis for the pitch rotation. Thus, as shown in FIG. 7, the yoke element 50 can pivot relative to the cup end 28 through a roll angle $\theta$, about an axis projecting from the page, whether rotating to one side or the other of the stationary element. As explained above, the amount of roll is limited by contact between the transition 63 and the opening 29 of the cup end 28. In a specific embodiment, the maximum roll angle $\theta$ is eleven degrees.

In addition to the pitch and roll degrees of freedom, the adjustable element 12 can also rotate about an axis extending upward between the branches 52 of the yoke element 50. Rotation in this yaw degree of freedom is essentially unlimited in the illustrated arrangements. The cross connector assembly 10 thus permits relative movement between the stationary element 12 and the adjustable element 14 in pitch, roll and yaw rotational degrees of freedom—i.e., about three mutually perpendicular axes—as well as axially along the length of the elongated bar 40 as it moves toward and away from the engagement end 12 of the stationary connector 12. It can be further appreciated that rotational movement is not limited to the three orthogonal planes or axes just described but may occur as a combination of pitch, roll and yaw. This multiple angular degree of freedom movement is augmented by the linear degree of freedom as the two connector elements can be moved closer together or farther apart by sliding the bar 40 relative to the yoke 50. Thus, the connector assembly permits pivoting simultaneously in different degrees of freedom as well as simultaneous relative linear movement and pivoting movement between the elements.

In an alternative approach, a cross connector assembly 110 includes a stationary element 112 that is identical to the element 12 described above. The stationary element 112 thus includes an engagement end 120 with a set screw 124 for clamping a rod. The element further includes a cup end 128 that is configured like the cup end 28 described above. The adjustable element 114 includes an engagement end 135 and set screw 139 that is similar to the element. However, in this arrangement the adjustable element 114 includes an extension member defined by an elongated plate 140 that defines an elongated slot 142 therethrough, rather than the elongated bar 40. The plate 140 sits on a locking collar 165 that can be configured like the locking collar 65.

In lieu of the yoke element 50, the cross connector assembly 110 includes a pivot element defined by an adjustment screw 150 that includes a threaded stem 152 sized to pass through the opening 129 in the cup end 128, through the locking collar 165 and through the slot 142 in the adjustable element. A nut 158 engages the threaded stem 152 to clamp the assembly together. The adjustment screw 150 includes an enlarged base 160 that incorporates a spherical surface 161 for articulating engagement with the cup end 128, as described above with respect to the yoke base 60. The adjustment screw 150 thus performs the same pivoting function as the yoke element by permitting variable angular articulating orientations in pitch, roll and yaw degrees of freedom. The locking collar 165 functions like the collar 65, and may be modified to incorporate a spring washer or wave washer between the collar and the underside of the plate 140 to provide temporary fixation. The plate 140 being generally flat provides for slidable but non-rotatable coupling to the adjustment screw 150 along the axis of the plate 140.

It can be appreciated that the cross connector disclosed herein is fully top-tightening. In other words, all of the clamping elements are accessible from directly above the cross connector to clamp the components together using a standard Allen or Torx® type wrench.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A cross connector for attachment between two spinal implants comprising:
   a first element having one end and an opposite end configured for engaging one of the two spinal implants;
   a second element having one end and an opposite end configured for engaging the other of the two spinal implants;
   an engagement mechanism between said one end of each of said first and second elements, said engagement mechanism having a spherical interface configured to permit relative pivoting between said first element and said second element simultaneously about three perpendicular axes, wherein said spherical interface includes an annular spherical surface at said one end of said first element, said annular spherical surface defining an opening therethrough, said one end of said first element including an annular spherical upper surface opposite said annular spherical surface, said engagement mechanism further including an annular collar having a lower spherical surface configured for pivoting movement on said spherical upper surface and an upper surface configured to support said one end of said second element thereon;
   an interface element having a base with a spherical surface configured for sliding pivoting contact with said annular spherical surface, and a locking portion extending from said base and sized to pass through said opening in said annular spherical surface; and
   a locking element for locking said first and second elements together at said respective one end, said locking element being configured for locking said second element to said locking portion when said locking portion extends through said opening;

wherein said one end of said second element includes a slotted plate defining an elongated slot, said locking portion of said interface element includes a locking post projecting from said base and sized to pass through said opening and said elongated slot; and said locking element is configured to engage said locking post when said locking post extends through said opening and said slot.

2. The cross connector of claim 1, wherein said first element includes an elongated bar between said one end and said opposite end, said bar defining a notch adjacent said annular upper spherical surface and sized to receive a portion of said annular collar therein when said collar is pivoted relative to said annular upper surface.

3. The cross connector of claim 1, in which at least one spinal implant is an elongated rod, wherein said opposite end of at least one of said first and second elements defines an opening sized to receive the rod therethrough and includes a set screw for clamping the rod within said opening.

4. The cross connector of claim , wherein said first element includes an elongated bar between said one end and said opposite end.

* * * * *

UNITED STATES PATENT AND TRADEMARK OFFICE
CERTIFICATE OF CORRECTION

| | |
|---|---|
| PATENT NO. | : 8,940,021 B2 |
| APPLICATION NO. | : 13/761342 |
| DATED | : January 27, 2015 |
| INVENTOR(S) | : Anthony James |

It is certified that error appears in the above-identified patent and that said Letters Patent is hereby corrected as shown below:

In the Specification

Column 1, line 4, replace "Application No. 61,179,790" with --Application No. 61/179,790--.

In the Claims

Column 7, line 19, replace "The cross connector of claim , wherein said first element" with --The cross connector of claim 1, wherein said first element--.

Signed and Sealed this
Second Day of June, 2015

Michelle K. Lee
*Director of the United States Patent and Trademark Office*